(12) United States Patent
Lading

(10) Patent No.: US 9,138,161 B2
(45) Date of Patent: Sep. 22, 2015

(54) METHODS, APPARATUS AND SENSOR FOR MEASUREMENT OF CARDIOVASCULAR QUANTITIES

(75) Inventor: Lars Lading, Roskilde (DK)

(73) Assignee: QUALCOMM Incorporated, San Diego, CA (US)

( * ) Notice: Subject to any disclaimer, the term of this patent is extended or adjusted under 35 U.S.C. 154(b) by 608 days.

(21) Appl. No.: 13/129,618

(22) PCT Filed: Nov. 18, 2009

(86) PCT No.: PCT/DK2009/000241
§ 371 (c)(1),
(2), (4) Date: May 17, 2011

(87) PCT Pub. No.: WO2010/057495
PCT Pub. Date: May 27, 2010

(65) Prior Publication Data
US 2011/0224529 A1    Sep. 15, 2011

(30) Foreign Application Priority Data

Nov. 18, 2008 (DK) .................................. 2008 01611

(51) Int. Cl.
*A61B 5/021* (2006.01)
*A61B 5/053* (2006.01)
(Continued)

(52) U.S. Cl.
CPC ................. *A61B 5/053* (2013.01); *A61B 5/021* (2013.01); *A61B 5/02007* (2013.01);
(Continued)

(58) Field of Classification Search
CPC .. A61B 5/02007; A61B 5/021; A61B 5/0218; A61B 5/02125; A61B 5/053; A61B 5/0537; A61B 5/6801; A61B 5/681; A61B 5/6824; A61B 5/6828; A61B 5/6831; A61B 5/6832; A61B 5/6833; A61B 2560/0412; A61B 2562/0214; A61B 2562/04; A61B 2562/164
USPC ......... 600/391, 392, 393, 485, 384, 382, 481, 600/500, 503, 506, 507, 547
See application file for complete search history.

(56) References Cited

U.S. PATENT DOCUMENTS 4,296,754 A * 10/1981 Hennig et al. ................. 600/507
4,448,199 A    5/1984 Schmid
(Continued)

FOREIGN PATENT DOCUMENTS

EP    0319160    6/1989
EP    0467853 A1    1/1992
(Continued)

OTHER PUBLICATIONS

U.S. Appl. No. 11/993,612, filed Apr. 2, 2008.
(Continued)

*Primary Examiner* — Lee S Cohen
*Assistant Examiner* — Erin M Cardinal
(74) *Attorney, Agent, or Firm* — The Marbury Law Group, PLLC

(57) ABSTRACT

The present disclosure relates to methods, apparatus and sensor for measurement of cardiovascular quantities. In particular, a method for determining one or more cardiovascular quantities is disclosed, the method comprising determining the distension of a vessel enclosed by tissue having a skin surface, wherein determining the distension is based on a first sensor signal indicating capacitance variations between a first electrode and a second electrode; determining the vascular stiffness of the vessel; and determining the blood pressure based on the distension and the vascular stiffness of the vessel.

18 Claims, 10 Drawing Sheets

(51) Int. Cl.
*A61B 5/00* (2006.01)
*A61B 5/02* (2006.01)

(52) U.S. Cl.
CPC ........ *A61B 5/02116* (2013.01); *A61B 5/02125* (2013.01); *A61B 5/681* (2013.01); *A61B 5/6822* (2013.01); *A61B 5/6824* (2013.01); *A61B 5/6833* (2013.01); *A61B 2562/0214* (2013.01)

(56) References Cited

U.S. PATENT DOCUMENTS

| | | | | |
|---|---|---|---|---|
| 4,562,843 | A * | 1/1986 | Djordjevich et al. | 600/485 |
| 4,807,638 | A * | 2/1989 | Sramek | 600/485 |
| 5,099,852 | A * | 3/1992 | Meister et al. | 600/485 |
| 5,199,438 | A | 4/1993 | Pearlman et al. | |
| 5,241,963 | A * | 9/1993 | Shankar | 600/481 |
| 5,309,916 | A * | 5/1994 | Hatschek | 600/485 |
| 5,551,437 | A * | 9/1996 | Lotscher | 600/485 |
| 5,647,369 | A | 7/1997 | Petrucelli et al. | |
| 5,830,131 | A | 11/1998 | Caro et al. | |
| 5,851,191 | A * | 12/1998 | Gozani | 600/554 |
| 5,904,654 | A * | 5/1999 | Wohltmann et al. | 600/481 |
| 6,015,386 | A | 1/2000 | Kensey et al. | |
| 6,015,387 | A | 1/2000 | Schwartz et al. | |
| 6,206,835 | B1 | 3/2001 | Spillman, Jr. et al. | |
| 6,261,233 | B1 * | 7/2001 | Kantorovich | 600/454 |
| 6,409,674 | B1 | 6/2002 | Brockway et al. | |
| 6,533,729 | B1 | 3/2003 | Khair et al. | |
| 6,554,773 | B1 | 4/2003 | Seppo et al. | |
| 6,558,225 | B1 | 5/2003 | Rehkemper et al. | |
| 6,807,438 | B1 * | 10/2004 | Brun Del Re et al. | 600/372 |
| 7,173,437 | B2 * | 2/2007 | Hervieux et al. | 324/663 |
| 7,245,956 | B2 * | 7/2007 | Matthews et al. | 600/382 |
| 2002/0055680 | A1 * | 5/2002 | Miele et al. | 600/450 |
| 2002/0151816 | A1 | 10/2002 | Rich et al. | |
| 2002/0188210 | A1 * | 12/2002 | Aizawa | 600/503 |
| 2003/0009111 | A1 * | 1/2003 | Cory et al. | 600/547 |
| 2003/0032993 | A1 | 2/2003 | Mickle et al. | |
| 2003/0060721 | A1 | 3/2003 | Nakazawa et al. | |
| 2003/0176808 | A1 * | 9/2003 | Masuo | 600/547 |
| 2004/0073104 | A1 * | 4/2004 | Brun del Re et al. | 600/372 |
| 2004/0133092 | A1 | 7/2004 | Kain | |
| 2004/0193058 | A1 | 9/2004 | Montegrunde et al. | |
| 2004/0220485 | A1 * | 11/2004 | Rytky | 600/509 |
| 2005/0015014 | A1 | 1/2005 | Fonseca et al. | |
| 2005/0054939 | A1 * | 3/2005 | Ben-Ari et al. | 600/506 |
| 2006/0211942 | A1 | 9/2006 | Hoctor et al. | |
| 2006/0224054 | A1 * | 10/2006 | Moriya et al. | 600/310 |
| 2007/0299330 | A1 * | 12/2007 | Couronne et al. | 600/368 |
| 2008/0262364 | A1 | 10/2008 | Aarts | |
| 2008/0287813 | A1 * | 11/2008 | Kirstein et al. | 600/488 |
| 2009/0209872 | A1 * | 8/2009 | Pop | 600/506 |
| 2010/0076328 | A1 | 3/2010 | Matsumura et al. | |
| 2010/0137724 | A1 | 6/2010 | Lading | |
| 2010/0268056 | A1 * | 10/2010 | Picard et al. | 600/388 |
| 2012/0184824 | A1 * | 7/2012 | Collette et al. | 600/301 |

FOREIGN PATENT DOCUMENTS

| | | |
|---|---|---|
| EP | 1344489 A1 | 9/2003 |
| EP | 1772702 A1 | 4/2007 |
| EP | 1798876 A1 | 6/2007 |
| FR | 2700683 A1 | 7/1994 |
| GB | 2367896 A | 4/2002 |
| WO | 94/16610 A2 | 8/1994 |
| WO | 02065905 A1 | 8/2002 |
| WO | 2004049937 A1 | 6/2004 |
| WO | 2007000164 A2 | 1/2007 |
| WO | 2007000164 A3 | 1/2007 |
| WO | 2008065873 A1 | 6/2008 |

OTHER PUBLICATIONS

International Search Report and Written Opinion—PCT/DK2009/000241—ISA/EPO—Jul. 8, 2010.

* cited by examiner

METHODS, APPARATUS AND SENSOR FOR MEASUREMENT OF CARDIOVASCULAR QUANTITIES

CROSS REFERENCE TO RELATED APPLICATIONS

This application is the national phase under 35 U.S.C. 371 of PCT International Application No. PCT/DK2009/000241 which has an international filing date of Nov. 18, 2009, and also claims priority under 35 U.S.C. 119 to Danish application PA 2008 01611 filed on Nov. 18, 2008, which applications are hereby incorporated by reference in their entirety for all purposes as if fully set forth herein.

The present invention relates to a method, apparatus and sensor for measuring one or more cardiovascular quantities, in particular vascular compliance, vascular stiffness and/or blood pressure. In particular, the invention relates to a method, apparatus and sensor for non-invasive, continuous measurement of vascular compliance, vascular stiffness, and/or blood pressure with a minimum of interference with the person.

BACKGROUND

Known methods for blood pressure measurements typically involve application of pressure from an external pressure device, e.g. occlusive cuff or other pressure generating devices. These interfering methods generating an external pressure may have a significant impact on the person and the blood pressure.

Blood pressure can be measured in a number of ways, such as invasive pressure sensor, oscillometric, auscultatory and tonometric. These methods will inevitably affect the state of the patient, e.g. require surgery or use of an occlusive cuff applying an external pressure to the artery. It has been reported that a considerable number of measurements performed at the office of a medical doctor or at a hospital are affected by the situation and may be quite erroneous compared to what would have been measured if the patient had not been affected by the medical environment. The golden standard for blood pressure measurement is an invasive pressure measurement implying considerable risk for the patient. The variations of the blood pressure in relation to the activity of the patient may provide very important information in relation to diagnosis.

Vascular compliance can be measured in a number of ways. An indirect method is based on evaluating the temporal shape of the blood pressure. Such method involves several assumptions, which may not be fulfilled. Ultrasound may be applied for direct wall displacement measurement. The ultrasound method relies on a good knowledge of the ultrasound velocity and at the same time characteristic acoustic propagation perturbations.

These methods are not suitable for ambulatory measurements. Thus, there is a need for a non-interfering scheme for measuring blood pressure and/or vascular compliance which scheme can be applied for ambulatory measurements and/or outside hospitals and other medical facilities.

Continuous monitoring of blood pressure has been reported to be an important parameter both in diagnostics and prognostics.

Non-invasive and non-interference methods for measuring vascular compliance and blood pressure generally suffer from the problem that too many assumptions about both dimensions, material properties, and curve shape of the temporal evolution of signals are needed in order to obtain useful measurements.

Existing methods do not provide non-interfering recording of blood pressure neither during sleep nor during physical activity.

SUMMARY

It is an object of the present invention to provide method and apparatus that are suitable for continuous monitoring of blood pressure of a living being under normal living conditions.

It is an object of the present invention to provide method and apparatus that are simple to use and which during use have minimum influence on the person or patient.

According to the invention, the above-mentioned and other objects are fulfilled by a method, in particular a method for determining one or more cardiovascular quantities, comprising determining the distension of a vessel. The method may comprise determining the vascular stiffness of the vessel, and may comprise determining the blood pressure based on the distension and the vascular stiffness of the vessel. Determining the distension of a vessel may be based on a first sensor signal indicating capacitance variations between a first electrode and a second electrode.

Further, an apparatus is provided, in particular an apparatus for measuring one or more cardiovascular quantities. The apparatus comprises a user interface, a processor connected to the user interface, and a memory connected to the processor. The processor may be configured for determining the distension and the vascular stiffness of a vessel. The processor may be configured for determining the blood pressure based on the distension and the vascular stiffness of the vessel.

The apparatus may comprise a reading unit for reading one or more sensor signals from one or more sensors.

In an aspect of the invention, a sensor is provided, wherein the sensor comprises a first electrode, a second electrode, and a carrier carrying the first electrode and the second electrode. The carrier may have a first electrically insulating layer with a first surface, the first electrically insulating layer insulating the first electrode and the second electrode from the first surface, wherein the shortest distance between the first electrode and the second electrode along the carrier is at least 3 cm.

In an aspect of the invention, a method for determining distension of a vessel enclosed by tissue having a skin surface is provided, comprising positioning a first electrode at a first position on the skin surface, positioning a second electrode at a second position on the skin surface such that lines of flux between the first electrode and the second electrode substantially extend through the vessel, measuring a sensor signal indicating capacitance variations between the first electrode and the second electrode, and determining distension of the vessel based on the sensor signal, comprising high pass filtering the sensor signal.

In an aspect of the invention, a method for determining vascular stiffness of a vessel is provided, comprising positioning a first electrode at a first position on a skin surface, positioning a second electrode at a second position on the skin surface such that lines of flux between the first electrode and the second electrode substantially extend through the vessel, positioning a third electrode at a third position on the skin surface such that lines of flux between the third electrode and the second electrode substantially extend through the vessel, performing measurements of pulse propagation velocity based on measurements of the capacitance between the electrodes, and determining vascular stiffness based on the performed measurements of the pulse propagation velocity. A fourth electrode may be positioned on the skin surface such that lines of flux between the third electrode and the fourth electrode substantially extend through the vessel.

It is an important advantage of the present invention that a non-interfering blood pressure measurement is enabled.

It is an important advantage of the present invention that the cardiovascular quantities, e.g. variations in the blood pressure, of a living being may be monitored with a minimum of influence on the person, e.g. without requiring application of external pressure.

It is an advantage of the present invention that a sensor, apparatus, system and method for non-invasive blood pressure measurement is provided.

It is an advantage of the present invention that a low cost sensor is provided.

It is a further advantage of the present invention that measurements in a non-medical environment are made possible.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

The figures are schematic and simplified for clarity, and they merely show details which are essential to the understanding of the invention, while other details have been left out. Throughout, the same reference numerals are used for identical or corresponding parts.

DETAILED DESCRIPTION

Figure 1:
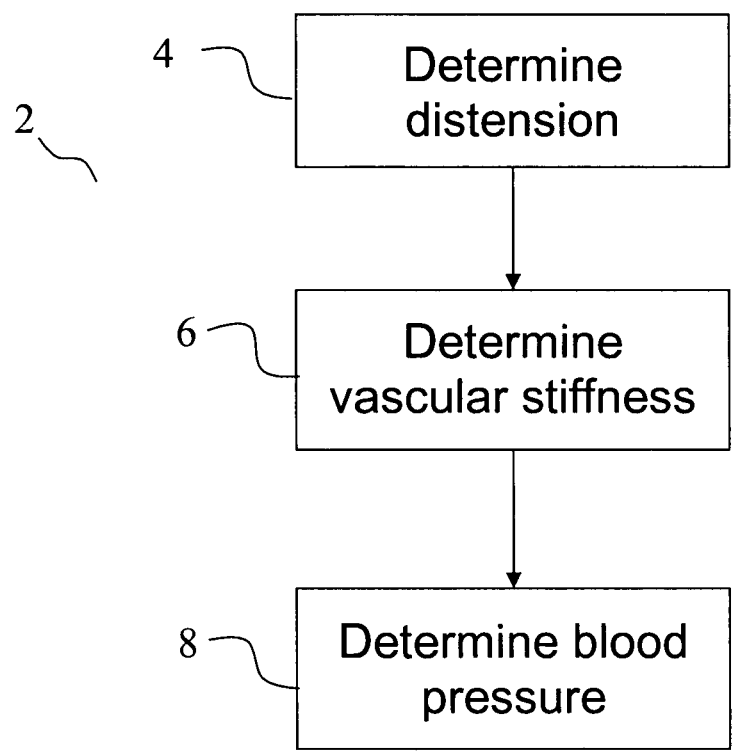
FIG. 1 is an exemplary flow diagram of a method according to the invention.

The method exploits the fact that the vascular diameter of a vessel changes in accordance with the instantaneous blood pressure. In order to convert a diameter change to a pressure, the stiffness of the vessel walls is needed. Pulse propagation in the walls of a vessel depends on the stiffness of the walls. By jointly measuring diameter changes and pulse propagation velocity both compliance and blood pressure can be determined. Accordingly, it is an important advantage of the method and apparatus that both compliance and blood pressure can be determined with a non-interfering measurement or recording of vessel properties, i.e. without interfering with the state of the vessels. Advantageously, the disclosed apparatus and method does not require complicated and expensive ultrasound equipment which is cumbersome to carry during daily activities. By jointly measuring distension and vascular stiffness it is possible to evaluate (calculate) the instantaneous blood pressure without calibration against a known reference.

The methods according to the invention exploit the fact that the capacitance of a capacitor depends on the dielectric constant of the medium between the plates of the capacitor. The dielectric constant of blood is different from the dielectric constant of tissue. Thus the capacitance between capacitor plates of a capacitor in between which an organ is placed will depend on the amount of blood and the amount of tissue. A change of the ratio of the two will cause a change of the capacitance.

The method for determining one or more cardiovascular quantities may, in addition to determining the blood pressure based on the distension and the vascular stiffness of the vessel, comprise determining vascular compliance based on corresponding values of the distension and the blood pressure.

The relation between the pressure and the relative change in radius of the vessel as a result of a pressure change can be rearranged to give the following relation:

$$\Delta P = \frac{\Delta r_{vessel}}{r_{vessel}} \frac{h_{vessel}}{r_{vessel}^2} E,$$

where $r_{vessel}$ is the vessel radius, h is the length of the vessel that is probed and is given by the electrode length, and E is the elastic modulus (vascular stiffness).

The elastic modulus can be obtained from the pulse wave velocity, which is given by the following expression (the Moens-Korteweg equation):

$$v = \sqrt{\frac{Eh}{2\rho r_{vessel}}}$$

where $\rho$ is the blood density. By measuring the pulse wave velocity, the elastic modulus can be obtained. If the pulse wave velocity is measured, then the vascular stiffness can be calculated.

Vascular compliance C is defined as the ratio of volume distension divided by pressure change and can readily be calculated when blood pressure change and distension is determined.

Determining the distension of a vessel may be based on a first sensor signal indicating capacitance variations, e.g. between a first electrode and a second electrode. The capacitance variations are synchronous with the pulse. The change in vessel volume can be calculated from the change in diameter when the dielectric constants of the constituents of the organ are known. A rigorous calculation has to be based on Maxwells equations (quasi-stationary), but simple calculation assuming plate-capacitors gives that $$\frac{\partial C}{\partial V_{vessel}} = \frac{\varepsilon_{vessel} - \varepsilon_{tissue}}{d^2} + \frac{A}{d}$$

where C is capacitance, d is the spacing between the electrodes, e is the dielectric constant, and A is the area of the electrode.

Determining the vascular stiffness of the vessel may be based on a first sensor signal and a second sensor signal.

The first sensor signal may indicate capacitance variations between a first electrode and a second electrode.

The second sensor signal may indicate capacitance variations between a third electrode and the second electrode.

The second sensor signal may indicate capacitance variations between the third electrode and a fourth electrode.

The method for determining one or more cardiovascular quantities may comprise recording a first sensor signal indicating capacitance variations between the first electrode and the second electrode. Recording the first sensor signal may comprise positioning the first electrode at a first position on the skin surface, and positioning the second electrode at a second position on the skin surface, preferably such that lines of flux between the first electrode and the second electrode substantially extend through the vessel.

The first positions and the second position may be any positions on a skin surface allowing lines of flux between the electrodes to extend through the vessel. In an embodiment, the first position and the second position are positions on opposite sides of a limb, e.g. an arm, a wrist, a leg. In an embodiment, the first position and the second position are positions on the neck of a person, e.g. with a distance larger than 2 cm along the skin surface. In an embodiment, the first position and the second position are positions on the chest of a person, e.g. with a distance larger than 2 cm along the skin surface.

Preferably, the first position is the inner wrist. Preferably, the second position is the outer wrist.

Determination of distension and vascular stiffness may comprise suitable signal processing of one or more sensor signals, e.g. including first and second sensor signals indicating capacitance variations between electrodes. The signal processing may comprise high pass filtering the first sensor signal, e.g. in order to filter away variations in capacitance due to bending or changes in outer diameter of the skin surface.

Vascular stiffness of the vessel may be determined in a number of ways. Preferably, determining the vascular stiffness of the vessel comprises determining pulse propagation velocity through the vessel. The pulse propagation velocity through the vessel may be determined by processing a first sensor signal and a second sensor signal indicating capacitance variations at different positions along the vessel. The pulse propagation velocity may be calculated based on the time difference between pulses and the distance between sensors.

The method for determining one or more cardiovascular quantities may comprise recording a second sensor signal indicating capacitance variations between two electrodes.

Recording the second sensor signal may comprise positioning a third electrode at a third position on the skin surface such that lines of flux between the third electrode and the second electrode substantially extend through the vessel. The third position may be at a predetermined distance from the first position upstream or downstream the vessel.

Recording the second sensor signal may comprise positioning a third electrode at a third position on the skin surface and a fourth electrode at a fourth position on the skin surface such that lines of flux between the third electrode and the fourth electrode substantially extend through the vessel.

An embodiment of the apparatus of the present invention may implement the method for determining one or more cardiovascular quantities. The processor of the apparatus may, in addition to determining the blood pressure based on the distension and the vascular stiffness of the vessel, be configured for determining vascular compliance based on corresponding values of the distension and the blood pressure.

FIG. 1 is a flow diagram illustrating an embodiment of a method according to the present invention. The method 2 for measuring one or more cardiovascular quantities comprises the step 4 of determining the distension of a vessel enclosed by tissue having a skin surface. Determination of the distension of the vessel is based on a first sensor signal indicating capacitance variations between a first electrode and a second electrode. Further, the method 2 comprises the step 6 of determining the vascular stiffness of the vessel. Determining the vascular stiffness of the vessel is based on the first sensor signal and a second sensor signal indicating capacitance variations between two electrodes, e.g. between the second electrode and a third electrode. Steps 4 and 6 may be performed in reverse order or simultaneously. The blood pressure is determined in step 8 based on the distension and the vascular stiffness of the vessel.

The vascular stiffness of the vessel is determined in step 6. Preferably, as illustrated, step 6 of determining the vascular stiffness of the vessel comprises determining pulse propagation velocity, e.g. based on recording of sensor signals indicating capacitance variations between electrodes at different positions along the vessel.

Figure 3:
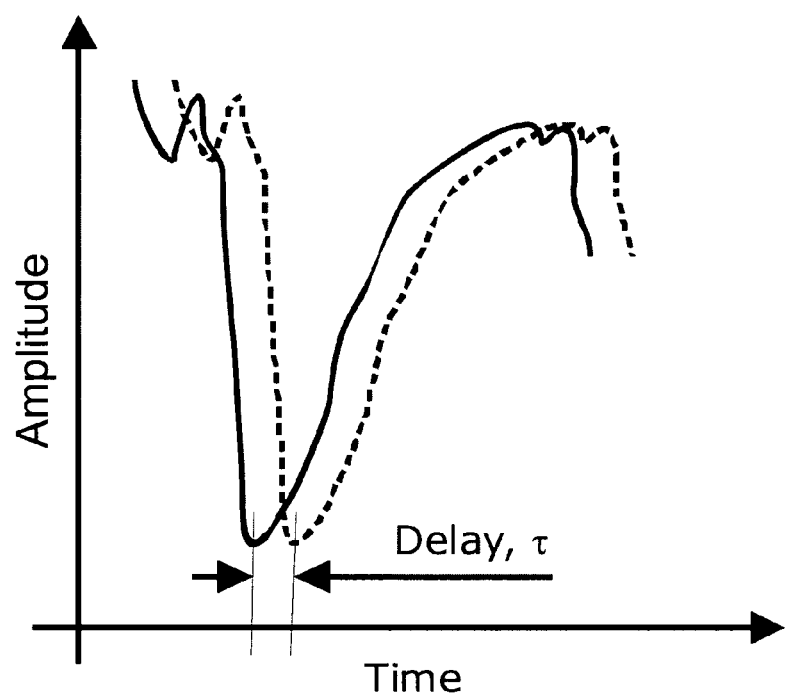
FIG. 3 shows a first sensor signal and a second sensor signal.

The pulse propagation velocity (ppv), which is much higher than the blood velocity or fluid velocity in the vessel, may be measured on the basis of a time of flight principle. One or more sensors which may be capacitive sensors as described, will record a first sensor signal and a second sensor signal that are temporally displaced as shown in FIG. 3, where the solid line is the first sensor signal and the dotted line is the second sensor signal. A first sensor, which may be a capacitive sensor as described, records a first sensor signal, and the first sensor or a second sensor, which may be a capacitive sensor as described, records a second sensor signal. The first sensor signal and the second sensor signal are temporally displaced as shown in FIG. 3, and the velocity v is then given by $$v = \frac{d_{ppv}}{\tau}$$

where $d_{ppv}$ is the distance along the vessel between two electrodes of the sensor(s), and $\tau$ is the delay between the first sensor signal and the second sensor signal. The first sensor and the second sensor may share a common electrode as reference, e.g. the second electrode.

The first and second sensor signals may be provided by a sensor comprising a first electrode, a second electrode, and a third electrode, wherein the first sensor signal indicates capacitance variations between the first electrode and the second electrode and the second sensor signal indicates capacitance variations between the third electrode and the second electrode. In such a sensor, the position of and thus the distance d between the first electrode and the third electrode is well-defined leading to a precise measurement of the pulse propagation velocity. The distance $d_{ppv}$ must be large enough to provide a delay with suitable precision, preferably $d_{ppv}$ is larger than 10 mm. Preferably, $d_{ppv}$ is selected less than 500 mm. In an embodiment, where the electrodes are incorporated in a single sensor, the distance $d_{ppv}$ may be in the range from about 10 mm to about 20 mm preferably from about 10 mm to about 15 mm, The first and second sensor signals may be provided by a first sensor and a second sensor, respectively.

Figure 2:
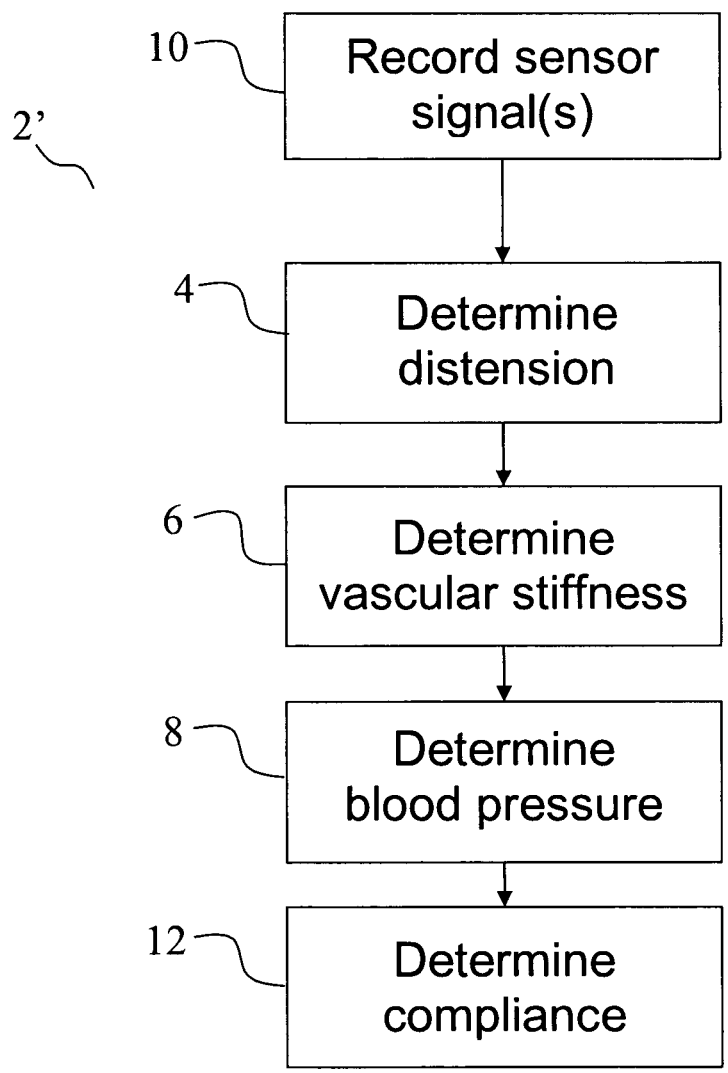
FIG. 2 is an exemplary flow diagram of a method according to the invention.

FIG. 2 illustrates an embodiment of the method according to the invention. The method 2' comprises the steps 4, 6, and 8 as described with reference to FIG. 1. Further, the method 2' comprises the step 10 of recording one or more sensor signals. Step 10 comprises recording a first sensor signal and a second sensor signal indicating capacitance variations between electrodes.

Step 10 of recording sensor signals comprises positioning a first electrode at a first position on the skin surface, and positioning a second electrode at a second position on the skin surface such that lines of flux between the first electrode and the second electrode substantially extend through the vessel. The first sensor signal indicates capacitance variations between the first electrode and the second electrode.

Further, step 10 of recording sensor signals may comprise positioning a third electrode at a first position on the skin surface, e.g. such that lines of flux between the third electrode and the second electrode substantially extend through the vessel. The second sensor signal indicates capacitance variations between the third electrode and the second electrode.

In an embodiment, a fourth electrode is positioned at a fourth position on the skin surface, and the fourth electrode is positioned such that lines of flux between the third electrode and the fourth electrode substantially extend through the vessel. The second sensor signal may indicate capacitance variations between the third electrode and the fourth electrode. The third and fourth electrode may be positioned at a predetermined distance from the first electrode and the second electrode upstream or downstream of the vessel, e.g. as shown in FIG. 11B.

Further, the method 2' for measuring one or more cardiovascular quantities comprises the step 12 of determining vascular compliance based on corresponding values of the distension and the blood pressure.

Figure 4:
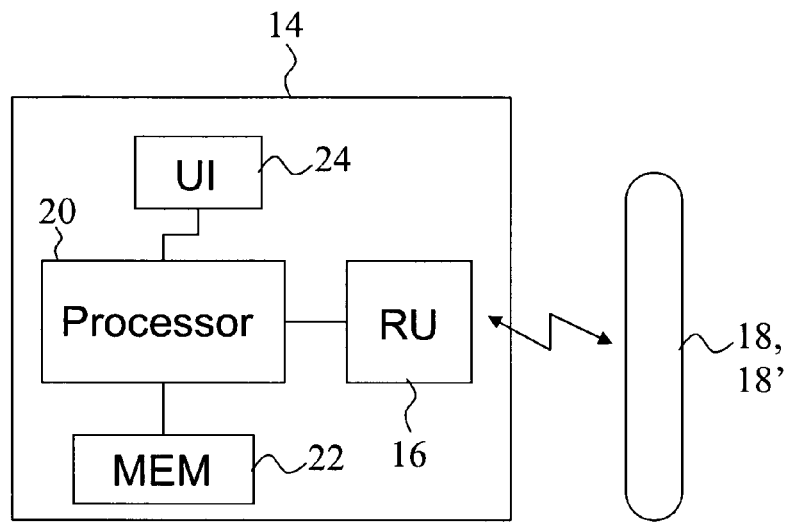
FIG. 4 schematically illustrates an apparatus according to the invention.

FIG. 4 illustrates an embodiment of an apparatus according to the invention. The apparatus 14 comprises a reading unit (RU) 16 for reading one or more sensor signals from one or more sensors 18, a processor 20 connected to the reading unit 16, and a memory (MEM) 22 connected to the processor 20. The processor 20 is configured for determining the distension and the vascular stiffness of a vessel, and determining the blood pressure based on the distension and the vascular stiffness of the vessel. Further, the apparatus 14 comprises a user interface (UI) 24. The user interface 24 may comprise a display for presenting information to a user. The user interface may comprise an input/output port for import/export of data.

The reading unit 16 may employ a capacitance detection principle based on an oscillator where the frequency changes in accordance with changes of the capacitance between the first electrode and the second electrode. However, other schemes for low-noise detection of very small changes in capacitance may also be applied.

Figure 5:
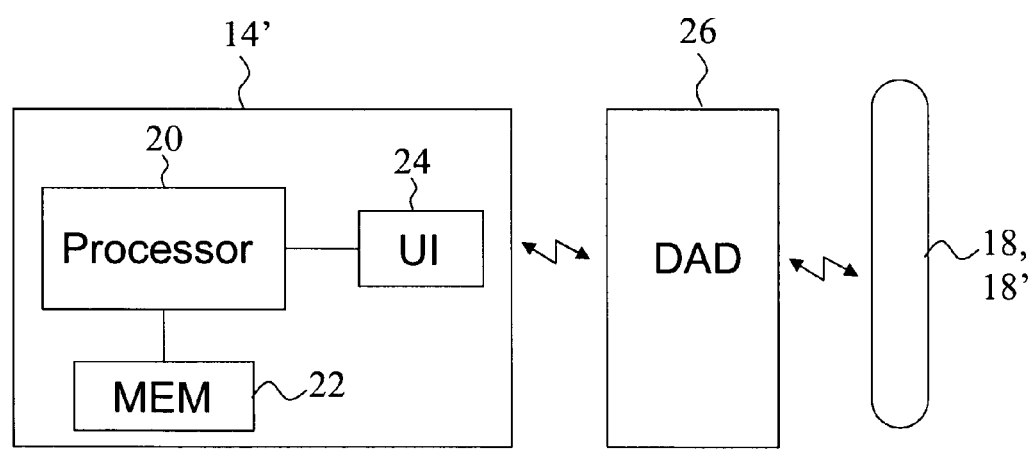
FIG. 5 schematically illustrates an apparatus according to the invention

FIG. 5 illustrates an embodiment of an apparatus according to the invention. The apparatus 14' comprises a processor 20, a memory (MEM) 22 connected to the processor 20, and a user interface (UI) 24. The processor 20 is configured for determining the distension and the vascular stiffness of a vessel, and determining the blood pressure based on the distension and the vascular stiffness of the vessel. The user interface 24 of apparatus 14' is configured for receiving data of a first sensor signal and a second sensor signal from a data acquisition device (DAD) 26 configured for recording one or more sensor signals from the sensor 18. The connection over which data between the apparatus 14' and the data acquisition device 26 is exchanged may be a wired or wireless connection. Further, the apparatus 14 comprises a user interface (UI) 24. The user interface 24 may comprise a display for presenting information to a user. The user interface may comprise an input/output port for import/export of data.

The sensor according to the invention may be flexible and capable of substantially contouring to the skin surface of a living being. The sensor may include rigid portions joined by flexible portions that allow the rigid portions to pivot with respect to one another to more closely contour to the skin surface.

The sensor may comprise a readout circuit having a first connection to the first electrode and a second connection to the second electrode. The readout circuit may be configured for reading changes in capacitance between the first electrode and the second electrode. Preferably, the readout circuit is configured for wireless communication with a data acquisition device or a reading unit of an apparatus according to the invention. The sensor may be a passive sensor, i.e. a sensor that does not require wired connection to a power supply, e.g. a battery, in order to operate correctly. Preferably, the sensor relies on passive components, such as capacitors, inductors, resistors, etc., for its operation.

In an embodiment of the present invention, the sensor is an active sensor, i.e. a sensor that is connected to a power supply, such as a battery or an energy harvesting device, e.g. a sun cell, etc. In an embodiment, the sensor may comprise a battery connected to the readout circuit.

The sensor may comprise a third electrode having a third connection to the readout circuit. The readout circuit may be configured for recording changes in capacitance between the third electrode and the second electrode.

The sensor may be formed of one or a plurality of layers stacked together to form the sensor.

The carrier may comprise a second layer, e.g. an electrically insulating layer. Electrodes, e.g. the first electrode, the second electrode and, if present, the third electrode, may be arranged between the first electrically insulating layer and the second layer. Electrodes, e.g. the first electrode, the second electrode and, if present, the third electrode may be embedded in the first electrically insulating layer.

The first electrode and the second electrode may be formed as plate electrodes of metal sheets having a suitable area. In an embodiment, the first electrode and the second electrode have an area of about 1 $cm^2$.

The first electrode may have an area from about 10 $mm^2$ to about 1600 $mm^2$, preferably about 100 $mm^2$ The second electrode may have an area from about 10 $mm^2$ to about 1600 $mm^2$, preferably about 100 $mm^2$.

The third electrode may have an area from about 10 $mm^2$ to about 1600 $mm^2$, preferably about 10 $mm^2$.

The sensor may be comprised in a sensor system comprising a data acquisition device configured for recording one or more sensor signals from the sensor.

A precise determination of pulse propagation velocity requires a well-defined positioning of the electrodes during measurements. In order to obtain such positioning, the sensor may comprise a surface adhesive, e.g. the first surface of the carrier may have an adhesive coating, for fastening or attaching the sensor to a skin surface in a way similar to application of a plaster. In an embodiment, the sensor may be fastened to the skin surface by a strap.

The design and construction of the sensor makes it possible to provide for a disposable sensor, i.e. the sensor may be disposable.

The sensor may have a substantially flat configuration in storage, and a curved or arcuate configuration in use.

Preferably, the sensor is an extra-corporal sensor, i.e. adapted for use outside the protecting membranes of the body of a living being.

Figure 6:
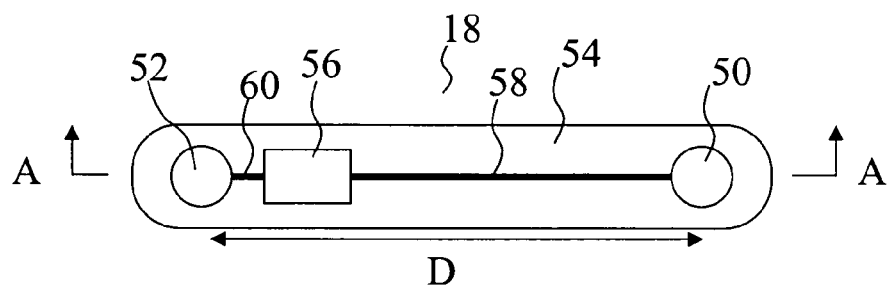
FIG. 6 is a plan view of an embodiment of the sensor according to the present invention.

FIG. 6 schematically illustrates an embodiment of the sensor according to the invention. The sensor 18 comprises a first electrode 50, a second electrode 52, and a carrier 54 carrying the first electrode 50 and the second electrode 52. The shortest distance D between the first electrode 50 and the second electrode 52 along the carrier is at least 3 cm. The electrode 18 is in particular suited for attachment around a wrist of a person. In the illustrated embodiment, the distance D is about 9 cm.

The distance D (center to center) between the first electrode and the second electrode may be larger than 3 cm, e.g. in the range from about 4 cm to about 15 cm. Preferably, the distance D ranges from about 5 cm to about 12 cm, more preferably between 7 and 10 cm.

The sensor 18 in FIG. 6 further comprises a readout circuit 56 having a first connection 58 to the first electrode 50 and a second connection 60 to the second electrode 52. The readout circuit 56 being configured for recording changes in capacitance between the first electrode 50 and the second electrode 52. The first 58 and second 60 connections provide an electrical path between the electrodes and the readout circuit.

Further, the readout circuit 56 is configured for wireless communication with a transceiver unit, e.g. the reading unit 16 or a data acquisition device 26, for reading out a first sensor signal indicative of changes in capacitance between the first electrode 50 and the second electrode 52. The sensor 18 is in particular useful in methods comprising determining distension of a vessel, e.g. methods 2, 2'. The first electrode 50 and the second electrode 52 each have an area of about 1 cm²

Figure 7:
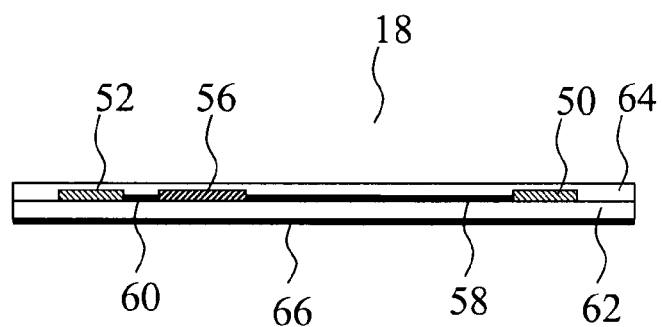
FIG. 7 is a cross section of an embodiment of the sensor of FIG. 6.
Figure 8:
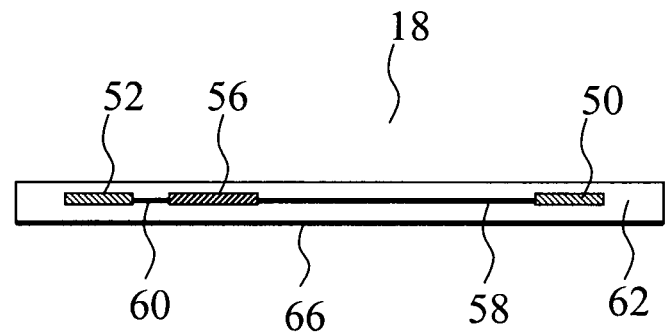
FIG. 8 is a cross section of an embodiment of the sensor of FIG. 6.

FIG. 7 illustrates a cross section of the sensor 18 along the line A indicated in FIG. 6. The electrodes, readout circuit and connections are enclosed between a first layer 62 of electrically insulating material and a second layer 64. The first surface of the carrier 54 has an adhesive coating 66 for attachment of the sensor to a skin surface. In an embodiment as illustrated in FIG. 8, the electrodes, readout circuit and connections are embedded in the first layer 62.

Figure 9:
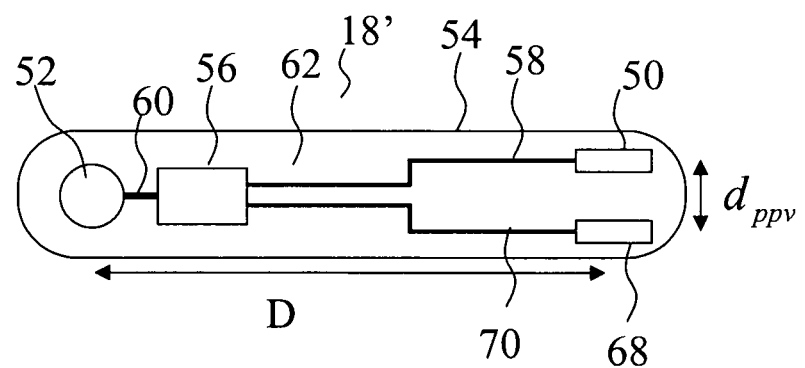
FIG. 9 is a plan view of an embodiment of the sensor according to the present invention, FIG. 10 schematically illustrates blood pressure measurement according to the present invention.

FIG. 9 schematically illustrates an embodiment of the sensor according to the invention. In addition to the elements 50, 52, 54, 56, 58, 60 described in connection with the sensor 18, the sensor 18' comprises a third electrode 68 connected by a third connection 70 to the readout circuit 56. The readout circuit 56 is configured for recording changes in capacitance between the third electrode 68 and the second electrode 52. Further, the readout circuit 56 is configured for wireless communication with a transceiver unit, e.g. the reading unit 16 or a data acquisition device 26, for reading out a second sensor signal indicative of changes in capacitance between the third electrode 68 and the second electrode 52.

In the sensor 18', the electrodes, readout circuit and connections may be enclosed between a first layer 62 of electrically insulating material and a second layer 64. The first surface of the carrier 54 has an adhesive coating 66 for attachment of the sensor to a skin surface. In an embodiment of the sensor 18', the electrodes, readout circuit and connections are embedded in the first layer 62.

The first electrode 50 and the third electrode 68 of the sensor 18' are positioned for enabling determination of pulse propagation velocity by a capacitive principle. The distance $d_{ppv}$ between the first electrode 50 and the third electrode 68 is used for determining the pulse propagation velocity of a pulse as described above. The distance (center to center) $d_{ppv}$ between the first electrode 50 and the third electrode may be more than 2 mm, preferably more than 4 mm. In the sensor 18' as illustrated, the distance $d_{ppv}$ is about 10 mm and the first electrode and the second electrode are plate electrodes having an area of about 0.5 cm².

The sensor 18' is in particular useful in methods comprising determining vascular stiffness of a vessel, e.g. the methods 2, 2'.

The sensor may comprise additional electrodes, e.g. used for reference measurements, positioned such that main field lines do not extend through large arteries, veins or parts disturbing measurements.

Figure 10:
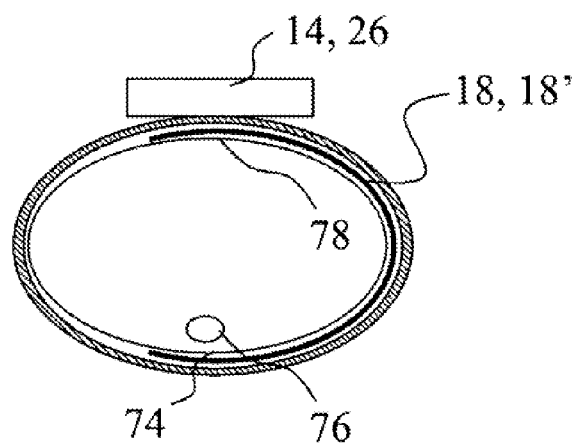

FIG. 10 illustrates use of the sensor and apparatus according to the invention. The sensor 18, 18' is attached around the wrist of a person. The sensor is attached to the skin surface by means of an adhesive coating on the first surface of the sensor such that the first electrode and, if present, the third electrode of the sensor are positioned on the inner wrist 74, preferably directly above the vessel 76, e.g. the ulnar or radial artery. The second electrode of the sensor is positioned on the outer wrist 78, i.e. on the opposite side of the first and third electrodes.

The sensor 18, 18' communicates wirelessly with the apparatus 14 or a data acquisition device 26 for transferring a first sensor signal and/or a second sensor signal to the apparatus 14 or data acquisition device 26. The first sensor signal and/or the second sensor signal may be processed in the apparatus 14 for determining the blood pressure and/or the compliance. The first sensor signal and/or the second sensor signal may be stored in the data acquisition device 26 and subsequently transferred to the apparatus 14' for determining the blood pressure and/or the compliance. The data acquisition device 26 may be configured for pre-processing the first sensor signal and/or the second sensor signal. Accordingly, pre-processed first and/or second sensor signal(s) may be transferred from the data acquisition device 26 to the apparatus 14'.

Figure 11A:
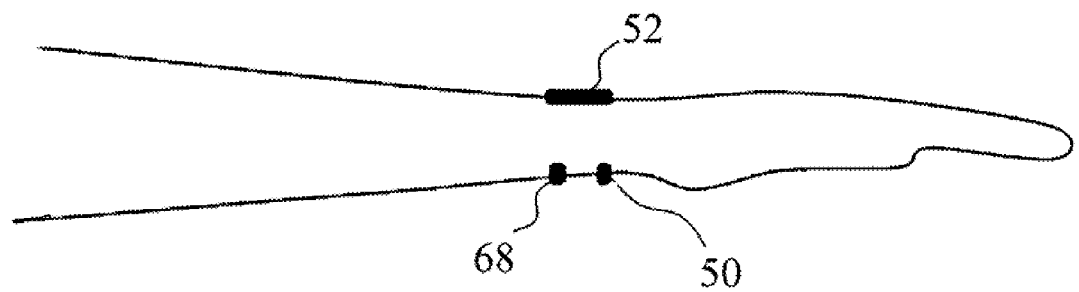
FIG. 11A illustrates exemplary positions of the electrodes on a wrist.
Figure 11B:
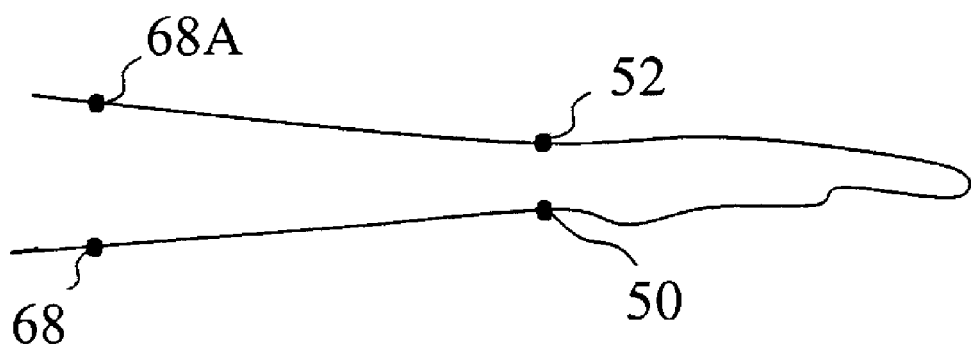
FIG. 11B illustrates exemplary positions of electrodes on a wrist.

FIG. 11A illustrates exemplary electrode positions on the wrist of a person. The first electrode 50 and the third electrode 68 are positioned on the inner wrist and the second electrode 52 is positioned on the outer wrist opposite the first and third electrodes 50, 68. The first sensor signal indicates capacitance variations between the first electrode and the second electrode, and the second sensor signal indicates capacitance variations between the third electrode and the second electrode.

FIG. 11B illustrates exemplary electrode positions on the wrist of a person. The first electrode 50 is positioned on the inner wrist and the second electrode 52 is positioned on the outer wrist opposite the first electrode 50. Further, a third electrode 68 is positioned on the inner arm and a fourth electrode 68A is positioned on the outer arm opposite the third electrode 68. The first set of electrodes 50, 52 and the second set of electrodes 68, 68A are positioned at a distance $d_{ppv}$ to enable measurement of the pulse propagation velocity. The first set of electrodes 50, 52 and the second set of electrodes 68, 68A may be embedded in a common sensor, e.g. sensor 18' with a fourth electrode 68A, or embedded in separate sensors with the first set of electrodes 50, 52 embedded in a first sensor, e.g. sensor 18, and the second set of electrodes 68, 68A embedded in a second sensor, e.g. sensor 18. The first sensor signal indicates capacitance variations between the first electrode and the second electrode, and the second sensor signal indicates capacitance variations between the third electrode and the fourth electrode.

Figure 12:
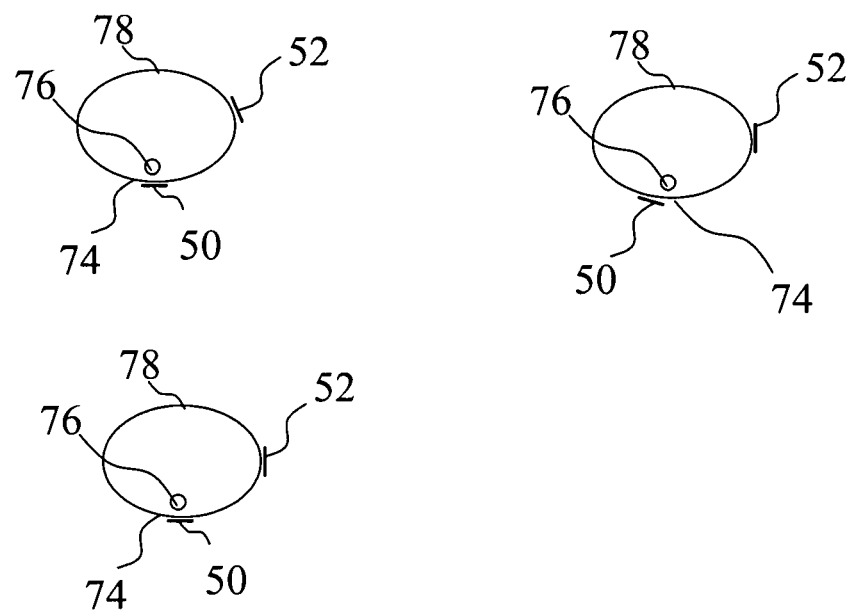
FIG. 12 illustrates exemplary positions of the electrodes on a wrist.

FIG. 12 illustrates exemplary electrode positions on the wrist of a person. The first electrode 50 is positioned on the inner wrist and the second electrode 52 is positioned on a side of the wrist such that lines of flux between the first electrode 50 and the second electrode 52 substantially extend through the vessel 76.

Figure 13:
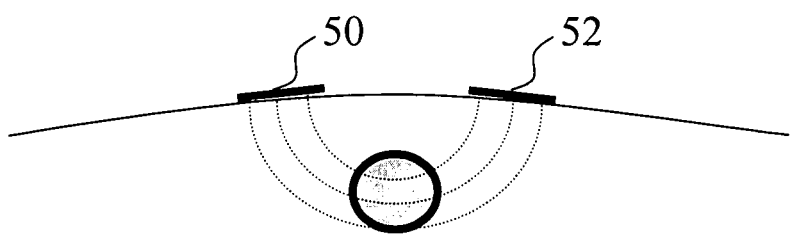
FIG. 13 illustrates exemplary positions of the electrodes on a neck.

FIG. 13 illustrates positioning of electrodes on a skin surface such as the neck of a person. The distance between the first electrode 50 and the second electrode 52 is 3 cm.

Figure 14:
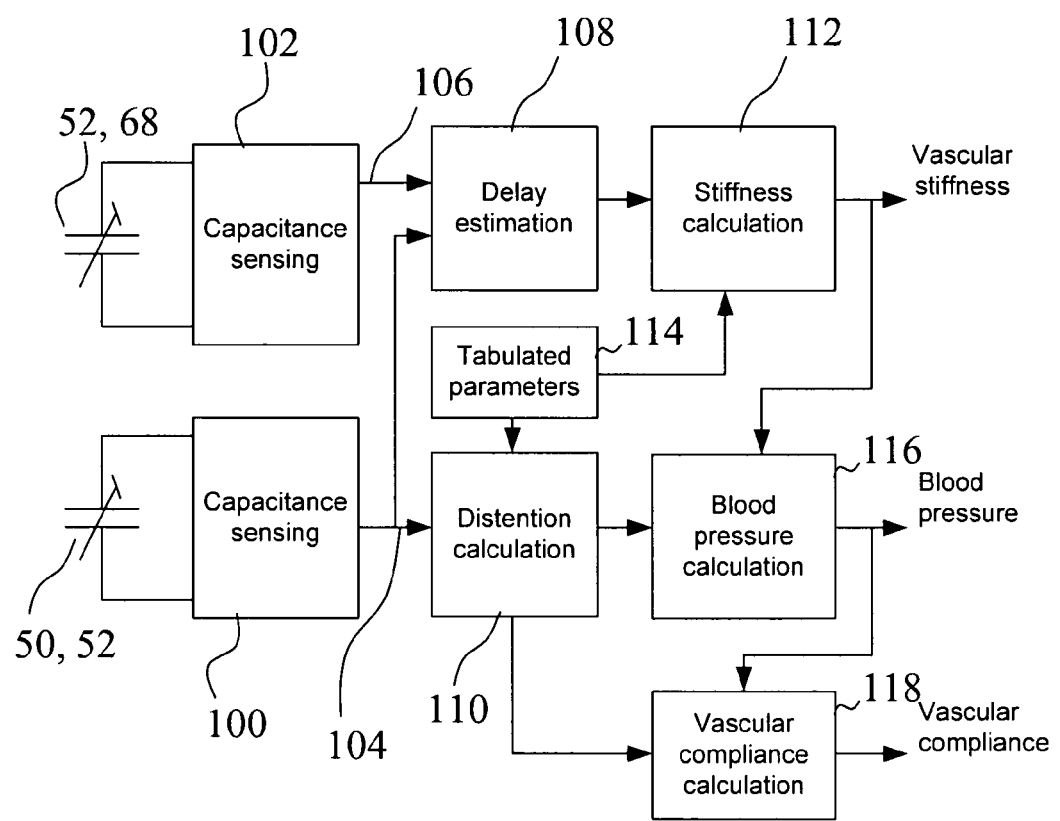
FIG. 14 illustrates a signal processing scheme employed in one or more embodiments of the present invention.

FIG. 14 illustrates a signal processing scheme employed in an embodiment of the present invention. The variations of the sensing capacitors formed by the electrodes are detected 100, 102. The capacitance sensing may be performed through resonant circuits, where changes in resonant frequencies are measured. The temporal variations of capacitance values, i.e. the first sensor signal 104 and/or the second sensor signal 106, are used for estimating delay 108 and distension 110. Delay estimation 108 can be performed by correlation and correlation fitting. The low frequency variations of the capacitances are removed and pulse shapes are estimated prior to calculation of vascular distension 110. Calculation of vascular stiffness 112 and distension 110 may be based on tabulated parameters 114 encoded in a table/memory. The tabulated parameters may include electrode parameters, anatomy parameters and/or material properties. The blood pressure is calculated 116 based on values of the vascular stiffness 112 and the distension 110. Finally, the vascular compliance is calculated 118 based on the blood pressure 116 and the distension 110.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

The invention claimed is:

1. A sensor for determining one or more cardiovascular quantities, comprising at least vascular stiffness of a vessel of a living being, the vessel being enclosed by tissue having a skin surface, comprising:
    said sensor being adapted for providing at least a first sensor signal indicating capacitance variations between electrodes in that the sensor comprises a first electrode at a first position and a second electrode at a second position with a distance D of at least 3 cm center to center between the first electrode and the second electrode, such that during use lines of flux between the first electrode and the second electrode substantially extend through and cross said vessel, and said sensor comprising a readout circuit having a first connection to the first electrode and a second connection to the second electrode, the readout circuit being configured for recording changes in capacitance between the first electrode and the second electrode, for a determination of a distension of the vessel based on at least said first sensor signal,
    said sensor being adapted for providing a second sensor signal indicating capacitance variations between electrodes, the sensor comprises
        a third electrode provided at a third electrode position adapted to be positioned at a predetermined distance ($d_{ppv}$) along the vessel from said first electrode, such that during use lines of flux substantially extend through and cross the vessel between said second electrode and said third electrode, and said third electrode having a third connection to said readout circuit, the readout circuit being configured for recording changes in capacitance between the third electrode and the second electrode, or
        a third electrode adapted to be displaced at a predetermined distance ($d_{ppv}$) along the vessel from said first electrode at a third electrode position and a fourth electrode at a fourth electrode position at the predetermined distance ($d_{ppv}$) from said first electrode such that lines of flux between the third electrode and the fourth electrode substantially extend through and cross the vessel, and said third electrode having a third connection to said readout circuit, the readout circuit being configured for recording changes in capacitance between the third electrode and the fourth electrode,
    wherein the sensor is adapted such that said first and second sensor signals are temporally displaced with a delay ($\tau$),
    wherein said sensor signals are suitable for performing determination of a pulse propagation velocity (v) based on a calculation of said predetermined distance ($d_{ppv}$) divided by said delay ($\tau$) between said first sensor signal and said second sensor signal, and
    wherein said sensor signals further are suitable for determining vascular stiffness based on the performed determination of the pulse propagation velocity (v).

2. A sensor according to claim 1, wherein the predetermined distance ($d_{ppv}$) is larger than 2 mm.

3. A sensor according to claim 1, comprising a carrier carrying said first electrode and said second electrode.

4. A sensor according to claim 3, said carrier having a first electrically insulating layer with a first surface wherein the first electrically insulating layer is insulating the first electrode and the second electrode from the first surface.

5. A sensor according to claim 4, wherein the carrier comprises a second layer and the first electrode and the second electrode are arranged between the first electrically insulating layer and the second layer.

6. A sensor according to claim 4, wherein the first electrode and the second electrode are embedded in the first electrically insulating layer.

7. A sensor according to claim 4, wherein the first surface of the carrier has an adhesive coating.

8. A sensor according to claim 3, wherein the carrier is a common carrier, and wherein said first electrode, said second electrode and said third electrode are embedded in the common carrier.

9. A sensor according to claim 1, wherein the first electrode and the second electrode are formed as plate electrodes of metal sheets having an area from 10 mm$^2$ to 1600 mm$^2$.

10. A sensor according to claim 1, wherein the sensor is flexible and capable of substantially contouring to the skin surface of the living being.

11. A sensor according to claim 1, comprising additional electrodes, adapted for reference measurements, and positioned such that main field lines do not extend through and cross large arteries, veins or parts disturbing measurements.

12. A blood pressure measurement system for determining one or more cardiovascular quantities, comprising at least vascular stiffness of a vessel of a living being, the vessel being enclosed by tissue having a skin surface, comprising a sensor according to claim 1 and an apparatus comprising a user interface, a processor connected to the user interface, and a memory connected to the processor, wherein the processor is configured for determining said distension of the vessel, and a reading unit for reading one or more sensor signals from said sensor readout circuit, wherein the system is configured to perform a method comprising:

positioning said first electrode at said first position on the skin surface, positioning said second electrode at said second position on the skin surface such that said lines of flux between said first electrode and said second electrode substantially extend through and cross the vessel and recording said first sensor signal indicating said capacitance variations between said first electrode and said second electrode for determining the distension of the vessel based on at least said first sensor signal, and either positioning said third electrode displaced at said predetermined distance ($d_{ppv}$) along the vessel from said first electrode at said third electrode position on the skin surface, such that said lines of flux between said third electrode and said second electrode substantially extend through and cross the vessel, and recording said second sensor signal indicating said capacitance variations between said second electrode and said third electrode, or positioning said third electrode displaced at said predetermined distance ($d_{ppv}$) along the vessel from said first electrode at said third electrode position on the skin surface and said fourth electrode at said fourth electrode position on the skin surface at the predetermined distance ($d_{ppv}$) from said second electrode such that said lines of flux between said third electrode and said fourth electrode substantially extend through and cross the vessel and recording said second sensor signal indicating said capacitance variations between said third electrode and said fourth electrode, wherein said first and second sensor signals are temporally displaced with said delay ($\tau$), and wherein the processor is configured for determining said pulse propagation velocity (v) based on said calculation of said predetermined distance ($d_{ppv}$) divided by said delay ($\tau$) between said first sensor signal and said second sensor signal, and wherein said processor further is adapted for determining said vascular stiffness based on said performed determination of said pulse propagation velocity (v).

13. A system according to claim 12, said processor further being configured for determining a blood pressure based on the distension and the vascular stiffness of said vessel.

14. A system according to claim 13, said processor further being configured for determining vascular compliance based on corresponding values of the distension and the blood pressure.

15. A method for determining one or more cardiovascular quantities, comprising at least vascular stiffness of a vessel of a living being, the vessel being enclosed by tissue having a skin surface, the method comprising:

positioning a first electrode at a first position on the skin surface, positioning a second electrode at a second position on the skin surface wherein a distance D from the second position to the first position is at least 3 cm such that lines of flux between the first electrode and the second electrode substantially extend through and cross the vessel and recording a first sensor signal indicating capacitance variations between said first electrode and said second electrode for determining a distension of the vessel based on at least said first sensor signal, and either positioning a third electrode displaced at a predetermined distance ($d_{ppv}$) along the vessel from said first electrode at a third electrode position on the skin surface, such that lines of flux between the third electrode and the second electrode substantially extend through and cross the vessel, and recording a second sensor signal indicating capacitance variations between said second electrode and said third electrode, or positioning said third electrode displaced at said predetermined distance ($d_{ppv}$) along the vessel from said first electrode at said third electrode position on the skin surface and a fourth electrode at a fourth electrode position on the skin surface at the predetermined distance along the vessel from said second electrode such that lines of flux between the third electrode and the fourth electrode substantially extend through and cross the vessel, and recording said second sensor signal indicating capacitance variations between said third electrode and said fourth electrode, wherein said first and second sensor signals are temporally displaced with a delay ($\tau$), determining a pulse propagation velocity (v) based on a calculation of said predetermined distance ($d_{ppv}$) divided by said delay ($\tau$) between said first sensor signal and said second sensor signal, and determining said vascular stiffness of said vessel based on the determined pulse propagation velocity (v).

16. A method according to claim 15, further comprising determining a blood pressure based on a combination of said determination of vascular stiffness of the vessel and said determination of the distension of said vessel.

17. A method according to claim 16, further comprising determining vascular compliance based on corresponding values of said distension and said blood pressure.

18. A method according to claim 15, wherein the first electrode position is at an inner wrist and the second electrode position an outer wrist or alternatively wherein the first electrode position and the second electrode position both are on a neck.

\* \* \* \* \*